United States Patent [19]

Otsuka et al.

[11] Patent Number: 5,178,628
[45] Date of Patent: Jan. 12, 1993

[54] SUTURE NEEDLE AND METHOD OF PRODUCING SAME

[75] Inventors: Tadashi Otsuka; Yoshimasa Tochimura, both of Tochigi, Japan

[73] Assignee: Matsutani Seisakusho Co., Ltd., Takanezawa, Japan

[21] Appl. No.: 679,189

[22] Filed: Apr. 2, 1991

[30] Foreign Application Priority Data

Apr. 5, 1990 [JP] Japan .................... 2-89116

[51] Int. Cl.$^5$ ............................ A61B 17/32
[52] U.S. Cl. ...................... 606/223; 606/222; 223/102; 163/5
[58] Field of Search .............. 606/223, 222; 163/5; 29/558, 557

[56] References Cited

U.S. PATENT DOCUMENTS

| 2,811,157 | 10/1957 | Kurtz et al. | 606/223 |
| 3,238,942 | 3/1966 | Lincoff | 606/223 |
| 3,636,955 | 1/1972 | Kurtz | 606/223 |
| 3,975,864 | 8/1976 | Glowacki | 51/165.87 |
| 4,128,351 | 12/1978 | Kurtz et al. | 606/223 |

FOREIGN PATENT DOCUMENTS 0107961  5/1984  European Pat. Off. .

Primary Examiner—Stephen C. Pellegrino
Assistant Examiner—Jeffrey A. Schmidt
Attorney, Agent, or Firm—Wegner, Cantor Mueller & Player

[57] ABSTRACT

In the production of a suture needle, a distal end portion of an elongated material is ground into a generally quadrangular pyramid shape. Then, the distal end portion of the elongated material is further ground into a generally triangular-pyramid shape, so that the distal or foremost end of the elongated material is positively pointed. The suture needle has four main surfaces and an auxiliary surface. The above triangular-pyramid shape is defined by two of the main surfaces and the auxiliary surface.

6 Claims, 6 Drawing Sheets

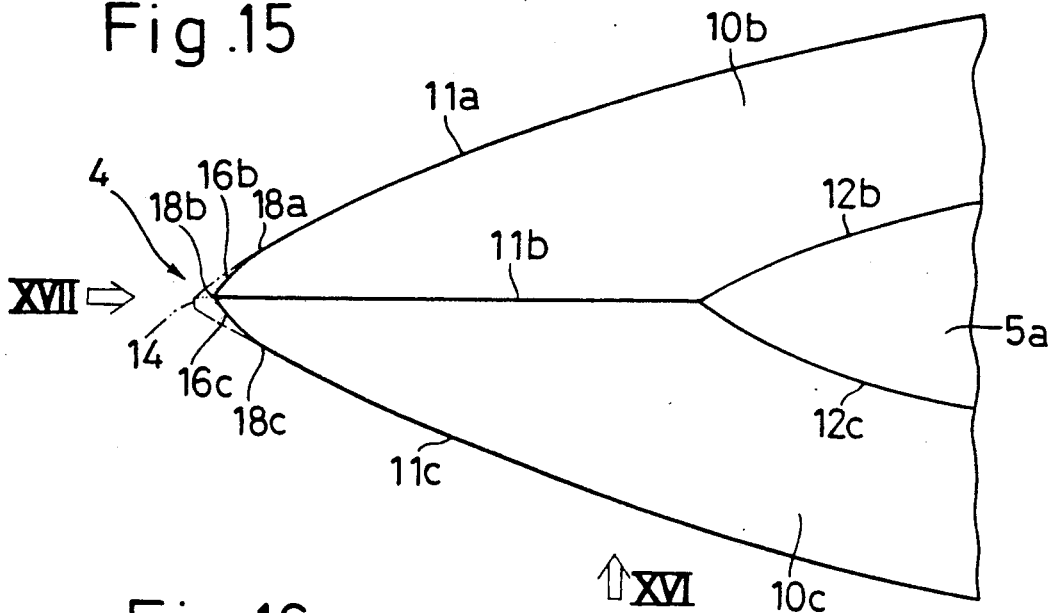
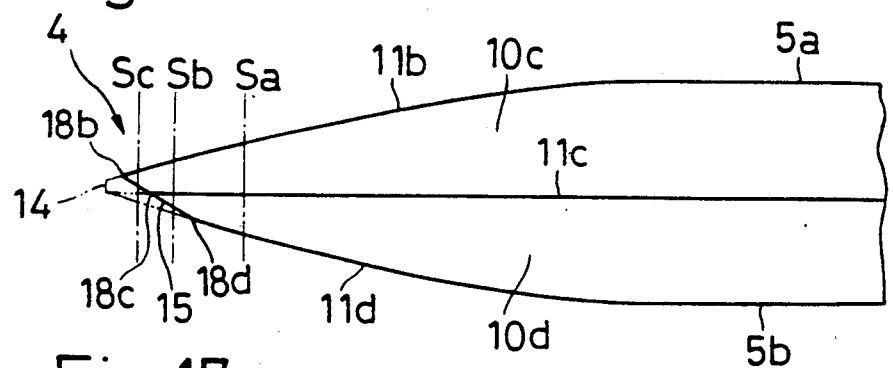
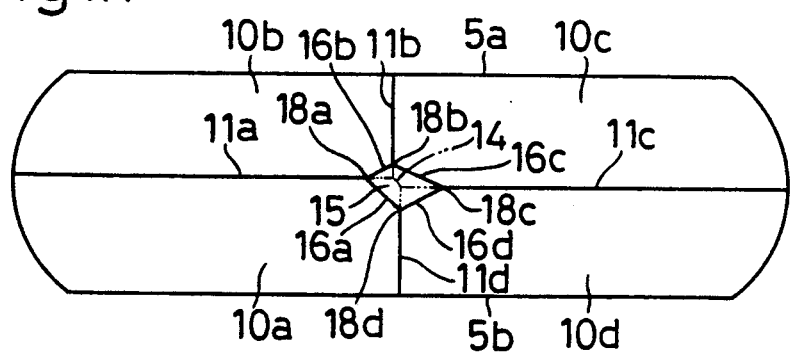
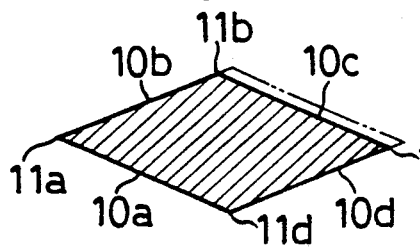
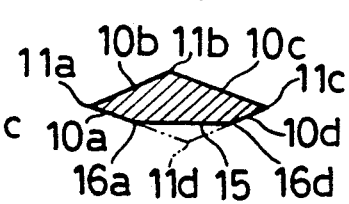
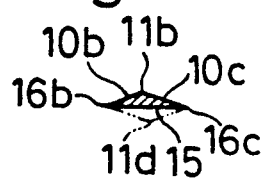

SUTURE NEEDLE AND METHOD OF PRODUCING SAME

BACKGROUND OF THE INVENTION

This invention relates to a suture needle having cutting edges and also to a method of producing such a suture needle.

There are well known suture needles whose distal end portion has a triangular, trapezoidal or rhombic cross-section, and has one or two cutting edges. Such various suture needles are used in accordance with the purpose of the surgical operation.

In order that the suture needle can have a good penetrating ability, the distal or foremost end thereof must be pointed. In a suture needle having a triangular cross-section as disclosed in Japanese Patent Publication No. 26783/89, its distal end portion is ground to form three ground surfaces so as to decrease the cross-sectional area of the distal end portion progressively toward the distal end of the suture needle. In this case, the foremost end of the suture needle is naturally pointed.

In a suture needle whose distal end portion has a quadrangular cross-section, when the distal end portion is to be ground to form four ground surfaces so as to decrease its cross-sectional area, the foremost end of the suture needle can be pointed only by precisely controlling the amount of grinding of each ground surface. For example, in a suture needle having a rhombic cross-section and having a pair of cutting edges, as disclosed in U.S. Pat. Nos. 1,506,262 and 3,238,942, the foremost end of the suture needle can be pointed when the amounts of grinding of the four ground surfaces are the same, and the pair of cutting edges intersect each other at this point. Otherwise, instead of such a pointed end, a short edge generally perpendicularly intersecting the longitudinal axis of the distal end portion is formed, and this edge intersects the cutting edges at its opposite end. In this case, the penetrating ability is worsened. Further, since the difference between the amount of actual grinding of each ground surface and the intended amount of grinding thereof varies from one suture needle to another, there occur variations in the penetrating ability. For controlling the grinding amount so as to form the foremost end of the suture needle into a pointed shape, the narrower the suture needle is, the higher precision is required, and the cost is increased.

Referring to other prior art, Japanese Patent Publication No. 57337/85 discloses a suture needle having a distal end portion pressed into a flattened configuration, and first, second and third ground surfaces are formed at this distal end portion, the second and third ground surfaces intersecting the first ground surface at an acute angle to form cutting edges. The cross-sectional area of the distal end portion of the suture needle is decreasing progressively toward the distal end thereof. The second and third ground surfaces do not intersect each other at that portion of the suture needle remote from the distal end thereof, and therefore this portion has a trapezoidal cross-section. The second and third ground surfaces intersect each other at that portion of the suture needle near the distal end thereof, and therefore this portion has a triangular cross-section. Further, an auxiliary ground surface is formed at the distal end portion of the suture needle, and this auxiliary ground surface intersects the second and third ground surfaces to make the foremost end pointed. The auxiliary ground surface serves to make the foremost point less sharp.

U.S. Pat. No. 4,128,351 discloses a suture needle in which a distal end portion of the suture needle is formed into a triangular cross-section by three ground surfaces. The angle between one ground surface and the axis of the distal end portion is greater than the angle of each of the other two ground surfaces and the axis of the distal end portion.

Japanese Utility Model Publication No. 6885/86 discloses a technique by which the grinding is carried out along a pair of cutting edges of a suture needle of a triangular cross-section, thereby forming another pair of cutting edges.

SUMMARY OF THE INVENTION

It is an object of this invention to provide a suture needle in which its foremost end is pointed while maintaining advantages achieved by a generally square cross-sectional shape of its distal end portion, thereby achieving a good penetrating ability.

Another object of the invention is to provide a method of producing such a suture needle.

According to one aspect of the present invention, there is provided a suture needle including a proximal end portion serving as a gut-attaching portion, a distal end portion whose cross-sectional area decreases progressively toward a distal end of the suture needle, and a main body portion lying between the proximal end portion and the distal end portion, the distal end portion including:

(a) first, second, third and fourth main surfaces formed on an outer periphery of the distal end portion and arranged sequentially around the periphery of the distal end portion, the first and second main surfaces intersecting each other to form a first main edge, the second and third main surfaces intersecting each other to form a second main edge, the third and fourth main surfaces intersecting each other to form a third main edge, and at least one of the first, second and third main edges serving as a cutting edge; and (b) an auxiliary surface formed on the distal end portion of the suture needle, the auxiliary surface intersecting the first, second, third and fourth main surfaces to form first, second, third and fourth auxiliary edges, respectively, the auxiliary surface intersecting the first, second and third main edges at their front ends to form first, second and third intersecting points, respectively, the second intersecting point being disposed forwardly of the first and third intersecting point, and serving as a foremost point of the suture needle, the foremost point being connected to the first main edge via the second auxiliary edge, and also being connected to the third main edge via the third auxiliary edge, that portion of the distal end portion disposed forwardly of the first and third intersecting points having a triangular-pyramid shape defined by the second and third main surfaces and the auxiliary surface, and that portion of the distal end portion disposed rearwardly of the first and third intersecting points having a pentagonal cross-sectional shape defined by the first, second, third and fourth main surfaces and the auxiliary surface.

According to another aspect of the invention, there is provided a method of producing a suture needle comprising the steps of:

(a) effecting main grinding by which a distal end portion of an elongated material is ground from four directions so as to decrease the cross-sectional area of the distal end portion progressively toward a distal end of the elongated material, thereby forming on an outer periphery of the distal end portion first, second, third and fourth main surfaces arranged sequentially around the periphery of the distal end portion, the first and second main surfaces intersecting each other to form a first main edge, the second and third main surfaces intersecting each other to form a second main edge, the third and fourth main surfaces intersecting each other to form a third main edge, and at least one of the first, second and third main edges serving as a cutting edge; and (b) subsequently effecting auxiliary grinding by which that portion of the distal end portion including front ends of the first, second, third and fourth main edges is ground to form an auxiliary surface, the auxiliary surface intersecting the first, second, third and fourth main surfaces to form first, second, third and fourth auxiliary edges, respectively, the auxiliary surface intersecting the first, second and third main edges at their front ends to form first, second and third intersecting points, respectively, the second intersecting point being disposed forwardly of the first and third intersecting points, and serving as a foremost point of the suture needle, and the foremost point being connected to the first main edge via the second auxiliary edge, and also being connected to the third main edge via the third auxiliary edge.

According to a further aspect of the invention, there is provided a method of producing a suture needle comprising the steps of:

(a) pressing a distal end portion and a main body portion of an elongated material of a generally circular cross-section into a flattened cross-sectional shape to thereby form a pair of parallel base surfaces on opposite sides of the flattened portions;

(b) effecting main grinding by which the distal end portion of the elongated material is ground from four directions so as to decrease the cross-sectional area of the distal end portion progressively toward a distal end of the elongated material, thereby forming on an outer periphery of the distal end portion first, second, third and fourth main surfaces arranged sequentially around the periphery of the distal end portion, the second and third main surfaces intersecting one of the pair of base surfaces, the first and fourth main surfaces intersecting the other base surface, the first and second main surfaces intersecting each other at an acute angle to form a first main edge, the second and third main surfaces intersecting each other at an obtuse angle to form a second main edge, the third and fourth main surfaces intersecting each other at an acute angle to form a third main edge, the first and fourth main surfaces intersecting each other at an obtuse angle to form a fourth main edge, and the first and third main edges serving cutting edges, respectively; and (c) subsequently effecting auxiliary grinding by which that portion of the distal end portion including front ends of the first, second, third and fourth main edges is ground to form an auxiliary surface, the auxiliary surface intersecting the first, second, third and fourth main surfaces to form first, second, third and fourth auxiliary edges, respectively, the auxiliary surface intersecting the first, second and third main edges at their front ends to form first, second and third intersecting points, respectively, the second intersecting point being disposed forwardly of the first and third intersecting point, and serving as a foremost point of the suture needle, and the foremost point being connected to the first main edge via the second auxiliary edge, and also being connected to the third main edge via the third auxiliary edge.

BRIEF DESCRIPTION OF THE DRAWINGS

FIG. 15 is an enlarged plan view of the distal end portion of the bar subjected to auxiliary grinding after the non-ideal main grinding is applied to the distal end portion;

FIG. 16 is a view as seen from arrow XVI of FIG. 15;

FIG. 17 is a view as seen from arrow XVII of FIG. 15;

FIGS. 18 to 20 are cross-sectional views taken along the lines Sa, Sb and Sc of FIG. 15, respectively;

DESCRIPTION OF THE PREFERRED EMBODIMENTS OF THE INVENTION

Figure 1:
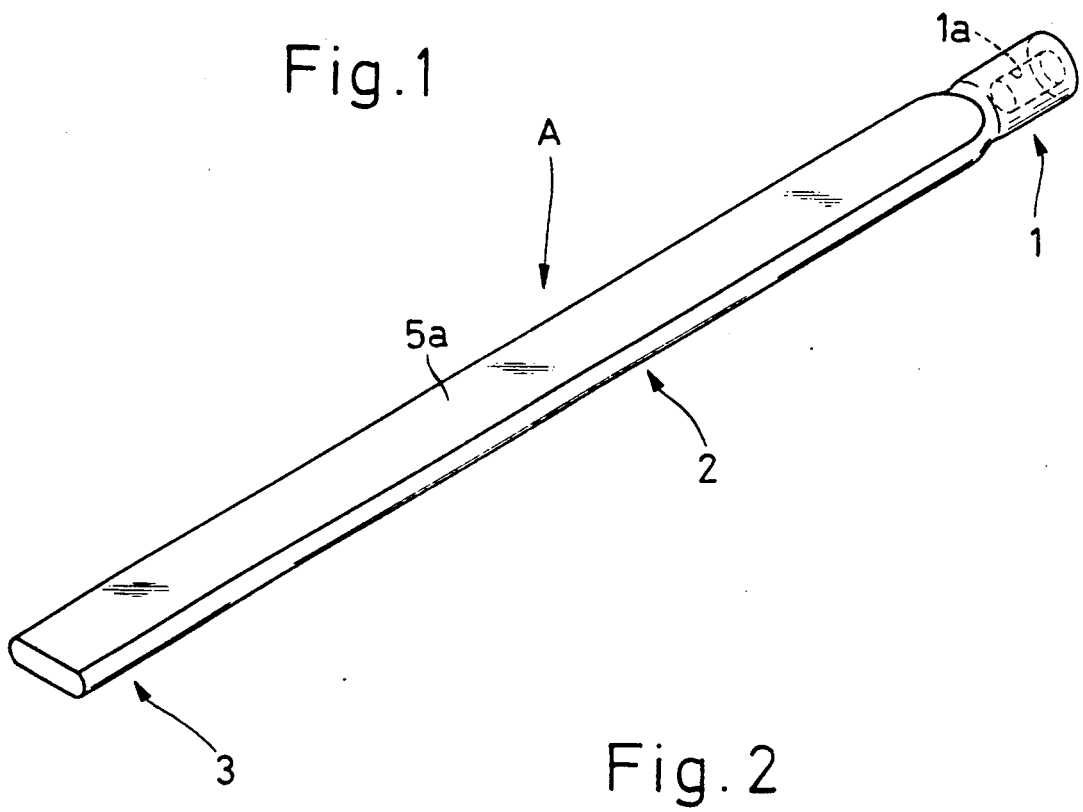
FIG. 1 is a perspective view of a bar subjected to pressing which is one step of a suture needle-producing method of the present invention.
Figure 2:
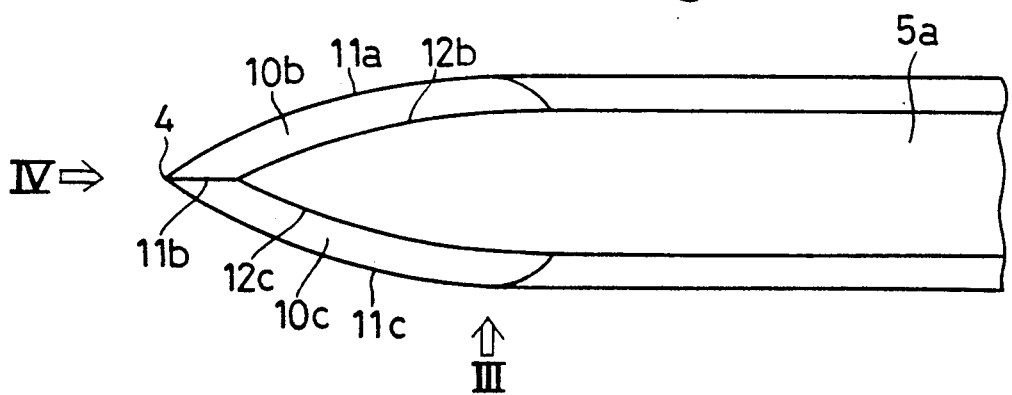
FIG. 2 is a plan view of a distal end portion of the bar subjected to main grinding.
Figure 3:
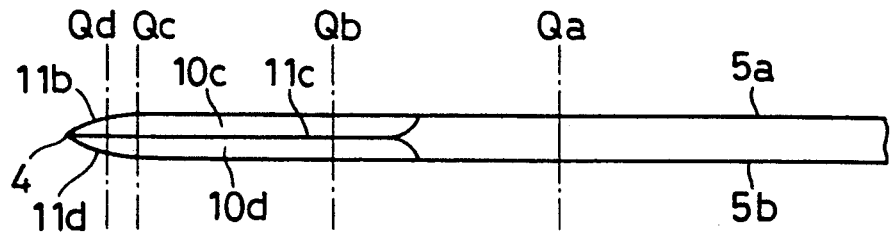
FIG. 3 is a view as seen from arrow III of FIG. 2.
Figure 4:
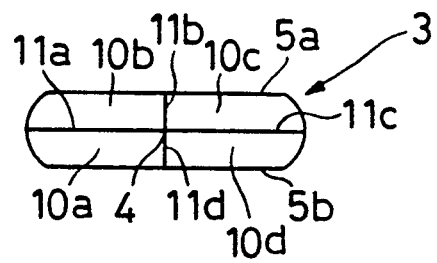
FIG. 4 is a view as seen from arrow IV of FIG. 2.
Figure 5:
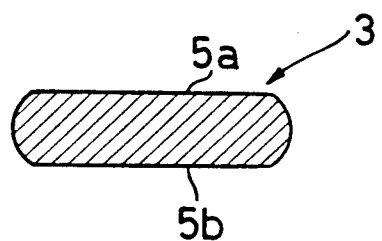
FIGS. 5 to 8 are cross-sectional views taken along the lines Qa, Qb, Qc and Qd of FIG. 3, respectively.

One preferred embodiment of a suture needle-producing method of the present invention will now be described with reference to the drawings. The suture needle produced by the method of this embodiment is used for an operation on the eye. A hole 1a for attaching a suture gut thereto is formed in one end portion (proximal end portion) 1 of a cross-sectionally circular bar (elongated material) A, as shown in FIG. 1. Then, except for the proximal end portion 1, the bar A (that is, a major body portion 2 and a distal end portion 3) is pressed into a flattened cross-sectional shape. As a result, the major body portion 2 and the distal end portion 3 have flat base surfaces 5a and 5b parallel to each other.

Then, as shown in FIGS. 2 to 8, main grinding is applied to the distal end portion 3. More specifically, the distal end portion 3 is ground from four directions to be formed into a tapered configuration, so that four (1st to 4th) main surfaces 10a, 10b, 10c and 10d are formed on the distal end portion and are arranged sequentially around the periphery of the distal end portion 3. The first and second main surfaces 10a and 10b are formed at one lateral edge portion of the distal end portion 3 whereas the third and fourth main surfaces 10c and 10d are formed at the other lateral edge portion of the distal end portion 3. The first and second main surfaces 10a and 10b intersect each other at an acute angle (for example, 40° to 45°) to form a first main edge 11a. Similarly, the third and fourth main surfaces 10c and 10d intersect each other at the same acute angle to form a third main edge 11c. The first main edge 11a and the third main edge 11c serve as cutting edges, respectively.

Figure 7:
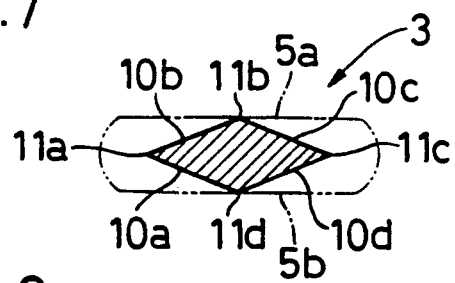
Figure 8:
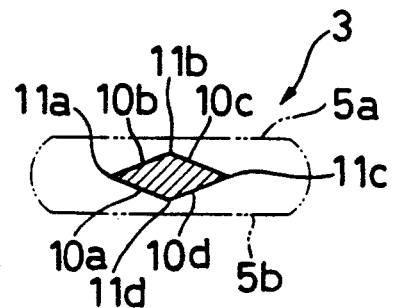

The second main surface 10b and the third main surface 10c intersect each other at an obtuse angle (135° to 140°) in the vicinity of a distal end 4 of the bar A, thereby forming a second main edge 11b. Similarly, the first main surface 10a and the fourth main surface 10d intersect each other at the same obtuse angle in the vicinity of the distal end 4, thereby forming a fourth main edge 11d. Therefore, that portion of the bar A where the four main surfaces 10a to 10d intersect one another has a generally quadrangular pyramid shape, and has the cross-section of a flattened rhombic shape as shown in FIGS. 7 and 8.

Figure 6:
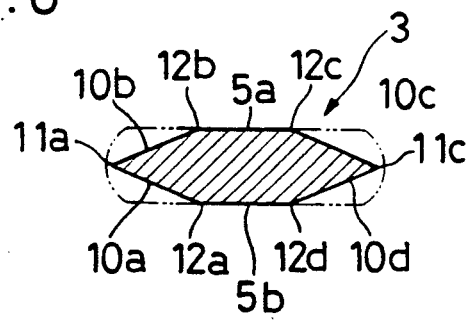

At that portion of the bar A remote from its distal end 4, the second main surface 10b and the third main surface 10c intersect one base surface 5a to form edges 12b and 12c, respectively. The edges 12b and 12c intersect each other at the rear end of the second main edge 11b. The first main surface 10a and the fourth main surface 10d intersect the other base surface 5b to form edges 12a and 12d, respectively. The edges 12a and 12d intersect each other at the rear end of the fourth main edge 11d. That portion of the distal end portion 3 disposed rearwardly of the rear ends of the second and fourth main edges 11b and 11d has a flattened hexagonal shape defined by the pair of base surfaces 5a and 5b and the four main surfaces 10a to 10d, as shown in FIG. 6.

Each of the four main surfaces 10a to 10d is convexly curved outwardly, and the main edges 11a to 11d as well as the edges 12a to 12d are also curved. However, the main surfaces 10a to 10d may be flat, and the main edges 11a to 11d as well as the edges 12a to 12d may be straight.

Figure 9:
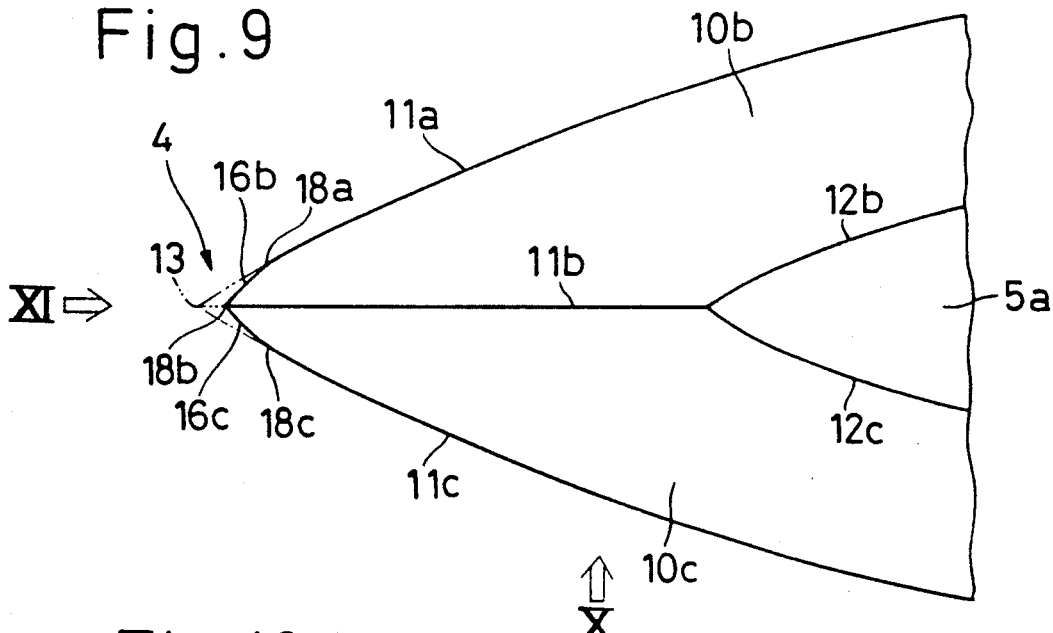
FIG. 9 is an enlarged plan view of the distal end portion of the bar subjected to auxiliary grinding after the ideal main grinding is applied to the distal end portion.
Figure 10:
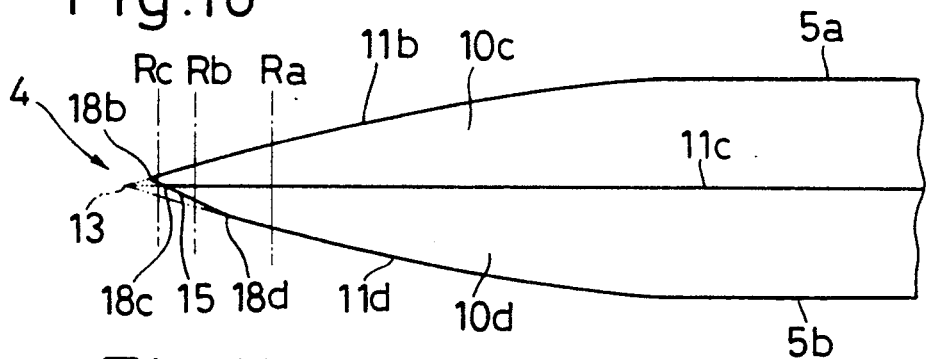
FIG. 10 is a view as seen from arrow X of FIG. 9.
Figure 11:
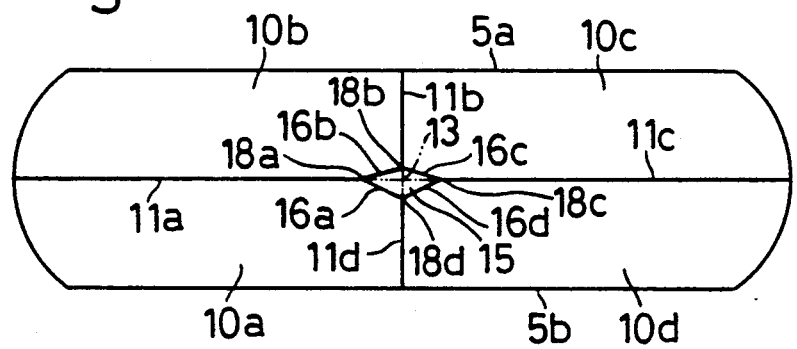
FIG. 11 is a view as seen from arrow XI of FIG. 9.

Next, the shape of the distal end 4 obtained by the above main grinding will now be described in detail. If the main grinding is carried out so ideally that the amounts of grinding of the four main surfaces 10a to 10d can be equal to one another, the four main surfaces 10a to 10d equally decrease in width progressively toward the distal end 4, and finally converge on a point 13, as shown in phantom in FIGS. 9 to 11.

If the amounts of grinding of the four main surfaces 10a, 10b, 10c and 10d are slightly different, for example, if the amount of grinding of one main surface 10c is larger than those of the other three main surfaces 10a, 10b and 10d with the result that the main surface 10c is disposed inwardly of its ideal position, as shown in phantom in an exaggerated manner in FIG. 18, the point 13 is not formed on the distal end 4. In this case, as shown in phantom in FIGS. 15 to 17, a short edge 14 generally perpendicularly intersecting the axis of the distal end portion 3 is formed. This edge 14 intersects the first and second main edges 11a and 11b at its one end, and also intersects the third and fourth main edges 11c and 11d at its other end. The existence of this edge 14 adversely affects the penetrating ability of the suture needle (final product).

In this embodiment, after the four main surfaces 10a to 10d are formed by the above main grinding, auxiliary grinding is carried out regardless of whether the distal end 4 has the ideal shape with the point 13 or the shape with the edge 14. More specifically, that portion of the bar A including the front ends of the four main edges 11a to 11d (that is, that portion in the vicinity of the front end 4) is slightly ground to form an auxiliary surface 15, as shown in FIGS. 9 to 11 or FIGS. 15 to 17, thereby removing the above point 13 or the above edge 14.

The auxiliary surface 15 is inclined relative to the axis of the distal end portion 3. The auxiliary surface 15 intersects the second and third main surfaces 10b and 10c at acute angles to form second and third auxiliary edges 16b and 16c. The auxiliary surface 15 intersects the first and fourth main surfaces 10a and 10d at obtuse angles to form first and fourth auxiliary edges 16a and 16d.

The auxiliary surface 15 intersects the four main edges 11a, 11b, 11c and 11d to form 1st to 4th intersecting points 18a, 18b, 18c and 18d. The second intersecting point 18b is disposed forwardly of the first and third intersecting points 18a and 18c, and serves as a foremost point of the suture needle as later described. The fourth intersecting point 18d is disposed rearwardly of the first and third intersecting points 18a and 18c. The foremost point 18b is connected to the first and third main edges 11a and 11c via the acute second and third auxiliary edges 16b and 16c.

Figure 12:
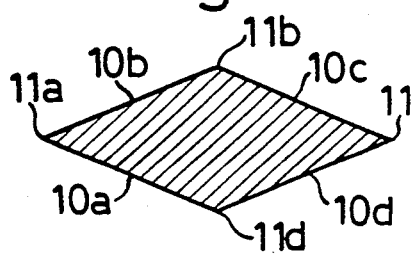
FIGS. 12 to 14 are cross-sectional views taken along the lines Ra, Rb and Rc of FIG. 10, respectively.
Figure 13:
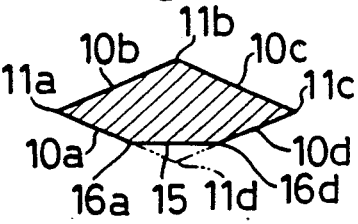
Figure 14:
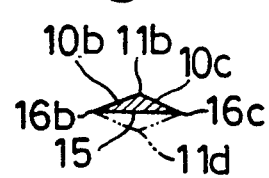

That portion of the distal end portion 3 disposed forwardly of the first and third intersecting points 18a and 18c has a triangular-pyramid shape defined by the second and third main surfaces 10b and 10c and the auxiliary surface 15, as shown in FIG. 14 or FIG. 20. Namely, this portion has a triangular cross-section, and decreases in cross-sectional area progressively toward the point 18b. That portion of the distal end portion 3 lying axially between the first and second intersecting points 18a and 18c and the fourth intersecting point 18d has a pentagonal cross-sectional shape defined by the four main surfaces 10a to 10d and the auxiliary surface 15, as shown in FIG. 13 or FIG. 19. That portion of the distal end portion 3 (where the auxiliary surface 15 is not provided) lying axially between the fourth intersecting point 18d and the rear ends of the second and fourth main edges 11b and 11d has a rhombic cross-sectional shape defined by the four main surfaces 10a to 10d, as shown in FIG. 12 or FIG. 18. Incidentally, if the main grinding for forming the main surfaces 10a to 10d is carried out not ideally with the result that the first and third intersecting points 18a and 18c are displaced relative to each other in the direction of the axis of the distal end portion 3, that portion of the distal end portion 3 lying between the intersecting points 18a and 18c has a square cross-section.

Figure 21:
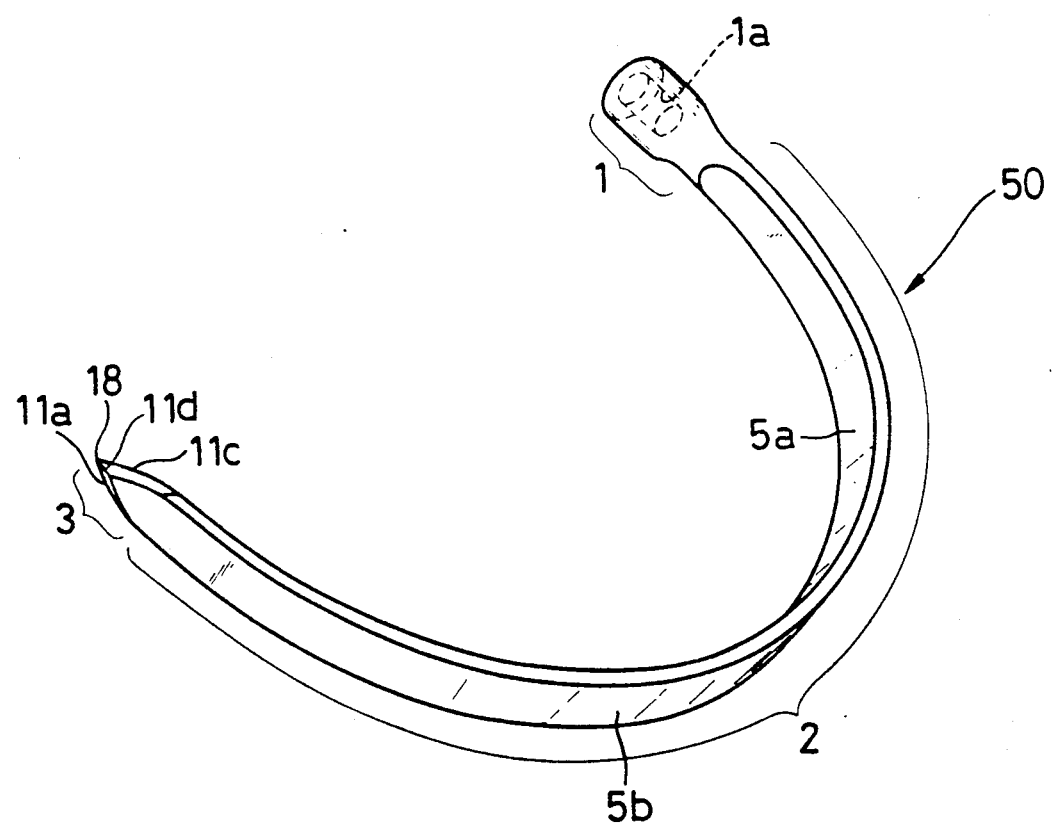
FIG. 21 is a perspective view of the suture needle in its finished form.
Figure 22:
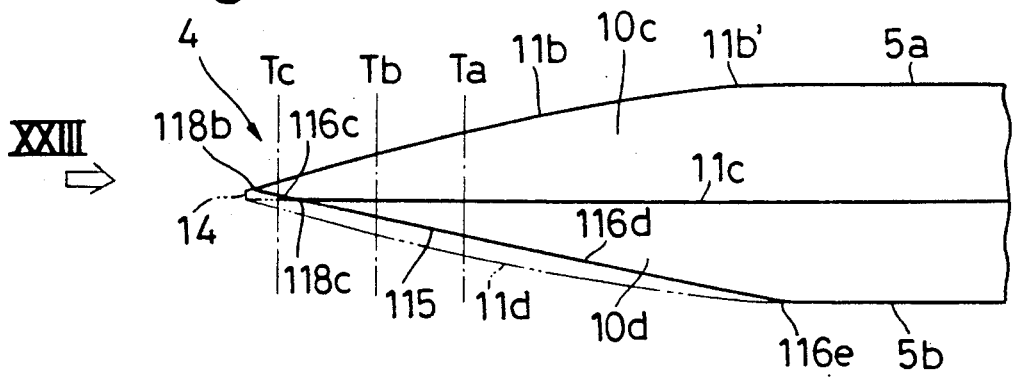
FIG. 22 is a front-elevational view of a distal end portion of a modified suture needle of the invention.
Figure 23:
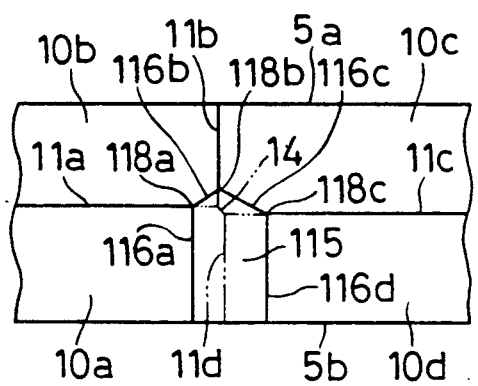
FIG. 23 is a view as seen from arrow XXIII of FIG. 22.

After the above auxiliary grinding is finished, the bar A is bent into a curved shape to obtain the suture needle 50 as shown in FIG. 21. In this case, the second main edge 11b is disposed on the inner side of the curved suture needle 50, and the fourth main edge 11d is disposed on the outer side of the curved suture needle 50. Then, the suture needle 50 is subjected to electrolytic polishing or chemical polishing if necessary, and then one end portion of the suture gut is inserted into the hole 1a, and the proximal end portion 1 of the suture needle 50 is deformed or compressed to fixedly hold the suture gut.

The distal end portion 3 of the suture needle of this embodiment is generally analogous in shape to the distal end portion of the above-mentioned conventional suture needle having a rhombic cross-section and having a pair of cutting edges. Therefore, the distal end portion 3 has the function similar to that of the distal end portion of this conventional suture needle. More specifically, the distal end portion 3 can advance while cutting the tissue by the pair of cutting edges 11a and 11c. That portion of the distal end portion 3 disposed forwardly of the intersecting points 18a and 18c is formed into a triangular-pyramid shape by providing the auxiliary surface 15, and therefore the foremost end of the suture needle 50 can be positively formed into the point 18b. This allows the suture needles to penetrate smoothly. Although the suture needle 50 is slightly inferior in penetrating ability to the type of suture needle in which the four main surfaces 10a to 10d are ideally formed, the difference in penetrating ability between the two is negligibly small.

The point 18b of the suture needle 50 is formed in the vicinity of the axis of the distal end portion 3, and is connected to the cutting edges 11a and 11c via the acute auxiliary edges 16b and 16c. With this arrangement, the good penetrating ability can be ensured. Further, the point 18b is formed on the front end of the second main edge 11b and is spaced generally equidistantly from the cutting edges 11a and 11c, and therefore during the surgical operation, the suture needle 50 is prevented from being displaced in the tissue in a direction generally transverse to the cutting edges, thus providing a good operability of the suture needle 50.

The above method of forming the point 18b by the provision of the auxiliary surface 15 can make the manufacturing cost lower as compared with the case where the main surfaces 10a to 10d are highly precisely controlled.

FIGS. 22 to 26 shows another embodiment of the invention. In this embodiment, the same main grinding as described above for the preceding embodiment is carried out. Those portions of this embodiment, formed by the main grinding and corresponding to those portions of the preceding embodiment, are designated respectively by identical reference numerals used in the preceding embodiment, and explanation thereof is omitted. In an auxiliary grinding operation, the grinding is carried out along a fourth main edge 11d to form an auxiliary surface 115. By this grinding, a point or an edge 14 on a distal end 4 is removed, and the fourth main edge 11d is also removed. The auxiliary surface 115 intersects a base surface 5b at its rear end to form a fifth auxiliary edge 116e generally perpendicularly intersecting the axis of the distal end portion 3. The auxiliary surface 115 intersects second and third main surfaces 10b and 10c to form acute second and third auxiliary edges 116b and 116c. The auxiliary edges 116b and 116c are acuter than the auxiliary edges 16b and 16c of the preceding embodiment. Also, the auxiliary surface 115 intersects first and fourth main surfaces 10a and 10d to form obtuse first and fourth auxiliary edges 116a and 116d. The first auxiliary edge 116a and the fourth auxiliary edge 116d are spaced from each other by the auxiliary surface 115 lying therebetween, and are generally parallel to each other. The auxiliary surface 115 intersects first, second and third main edges 11a, 11b and 11c to form first, second and third intersecting points 118a, 118b and 118c. The second intersecting point 118b serves as a foremost point of the suture needle.

Figure 24:
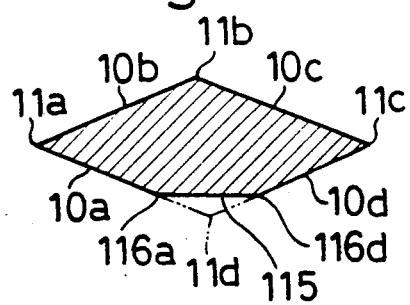
FIGS. 24 to 26 are cross-sectional views taken along the lines Ta, Tb and Tc of FIG. 23, respectively.
Figure 25:
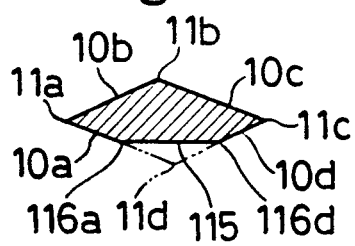
Figure 26:
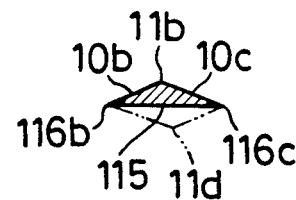

That portion of the distal end portion 3 disposed forwardly of the first and third intersecting points 118a and 118c has a triangular-pyramid shape defined by the second and third main surfaces 10b and 10c and the auxiliary surface 115, and has a triangular cross-section as shown in FIG. 26. That portion of the distal end portion 3 lying between the first and third intersecting points 118a and 118c and a rear end 11b' of the second main edge 11b has a pentagonal cross-sectional shape defined by the four main surfaces 10a to 10d and the auxiliary surface 115, as shown in FIGS. 24 and 25. That portion of the distal end portion 3 lying between the rear end 11b' of the second main edge 11b and the fifth auxiliary edge 116e has a hexagonal cross-sectional shape defined by one base surface 5a, the auxiliary surface 115 and the four main surfaces 10a to 10d. That portion of the distal end portion 3 disposed rearwardly of the fifth auxiliary edge 116e has a hexagonal cross-sectional shape defined by the pair of base surfaces 5a and 5b and the four main surfaces 10a to 10d. Incidentally, if the first and third intersecting points 118a and 118c are displaced relative to each other in the direction of the axis of the distal end portion 3, that portion of the distal end portion 3 lying between the intersecting points 18a and 18c has a square cross-section.

The present invention is not limited to the above embodiments, and various modifications can be made. For example, the major body portion of the bar may not be flattened, but may have a circular cross-section. The angle of intersection between the first and second main surfaces, as well as the angle of intersection between the third and fourth main surfaces, may be about 60°. The proximal end portion of the suture needle may be pressed into a flattened shape, and a gut-attaching hole may be formed in this flattened proximal end portion so as to extend perpendicular to the axis thereof.

Figure 27:
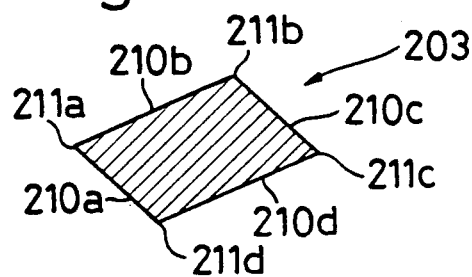
FIG. 27 is a view similar to FIG. 12, but showing another modified form of the invention.

As shown in FIG. 27, the main grinding may be carried out to form a distal end portion 203 into a parallelogrammatic shape, so that the width of first and third main surfaces 210a and 210c is smaller than the width of second and fourth main surfaces 210b and 210d. In this case, also, a pair of cutting edges 211a and 211c as well as a pair of obtuse edges 211b and 211d are formed.

What is claimed is:

1. A suture needle including a proximal end portion serving as a gut-attaching portion, a distal end portion whose cross-sectional area decreases progressively toward a distal end of said suture needle, and a main body portion lying between said proximal end portion and said distal end portion, said distal end portion including:

(a) first, second, third and fourth main surfaces formed on an outer periphery of said distal end portion and arranged sequentially around the periphery of said distal end portion, said first and second main surfaces intersecting each other to form a first main edge, said second and third main surfaces intersecting each other to form a second main edge, said third and fourth main surfaces intersecting each other to form a third main edge, said first and second main surfaces intersecting each other at an acute angle so that said first main edge serves as a main cutting edge, said third and fourth main surfaces intersecting each other at an acute angle so that said third main edge also serves as another main cutting edge;

(b) an auxiliary surface formed on said distal end portion of said suture needle, said auxiliary surface intersecting said first, second, third and fourth main surfaces to form first, second, third and fourth auxiliary edges, respectively, said second and third auxiliary edges serving as auxiliary cutting edges which are sharper than said main cutting edges, said auxiliary surface intersecting said first, second and third main edges at their front ends to form first, second and third intersecting points, respectively, said second intersecting point being disposed forwardly of said first and third intersecting point, and serving as a foremost point of said suture needle, said foremost point being connected to said first main edge via said second auxiliary edge, and also being connected to said third main edge via said third auxiliary edge, that portion of said distal end portion disposed forwardly of said first and third intersecting points having a triangular-pyramid shape defined by said second and third main surfaces and said auxiliary surface, and that portion of said distal end portion disposed rearwardly of said first and third intersecting points having a pentagonal cross-sectional shape defined by said first, second, third and fourth main surfaces and said auxiliary surface, in which said first and fourth auxiliary edges are spaced from each other by said auxiliary surface lying therebetween.

2. A suture needle including a proximal end portion serving as a gut-attaching portion, a distal end portion whose cross-sectional area decreases progressively toward a distal end of said suture needle, and a main body portion lying between said proximal end portion and said distal end portion, said distal end portion including:

(a) first, second, third and fourth main surfaces formed on an outer periphery of said distal end portion and arranged sequentially around the periphery of said distal end portion, said first and second main surfaces intersecting each other to form a first main edge, said second and third main surfaces intersecting each other to form a second main edge, said third and fourth main surfaces intersecting each other to form a third main edge, said first and second main surfaces intersecting each other at an acute angle so that said first main edge serves as a main cutting edge, said third and fourth main surfaces intersecting each other at an acute angle so that said third main edge also serves as another main cutting edge;

(b) an auxiliary surface formed on said distal end portion of said suture needle, said auxiliary surface intersecting said first, second, third and fourth main surfaces to form first, second, third and fourth auxiliary edges, respectively, said second and third auxiliary edges serving as auxiliary cutting edges which are sharper than said main cutting edges, said auxiliary surface intersecting said first, second and third main edges at their front ends to form first, second and third intersecting points, respectively, said second intersecting point being disposed forwardly of said first and third intersecting point, and serving as a foremost point of said suture needle, said foremost point being connected to said first main edge via said second auxiliary edge, and also being connected to said third main edge via said third auxiliary edge, that portion of said distal end portion disposed forwardly of said first and third intersecting points having a triangular-pyramid shape defined by said second and third main surfaces and said auxiliary surface, and that portion of said distal end portion disposed rearwardly of said first and third intersecting points having a pentagonal cross-sectional shape defined by said first, second, third and fourth main surfaces and said auxiliary surface;

wherein said main body portion and said distal end portion have a pair of base surfaces substantially parallel to each other, one of said pair of base surfaces intersecting said second and third main surfaces at said distal end portion, and the other base surface intersecting the first and fourth main surfaces at said distal end portion; and wherein the angle of intersection between said first and second main surfaces is generally equal to the angle of intersection between said third and fourth main surfaces, said first and fourth auxiliary edges being spaced from each other by said auxiliary surface lying therebetween, said auxiliary surface intersecting said other base surface to form a fifth auxiliary edge extending generally perpendicular to the axis of said distal end portion, said fifth auxiliary edge being disposed rearwardly of the rear end of said second main edge, that portion of said distal end portion lying between said first and third intersecting points and the rear end of said second main edge having a pentagonal cross-sectional shape defined by said auxiliary surface and said first, second, third and fourth main surfaces, that portion of said distal end portion lying between the rear end of said second main edge and said fifth auxiliary edge having a hexagonal cross-sectional shape defined by said one base surface, said auxiliary surface and said first, second, third and fourth main surfaces, and that portion of said distal end portion disposed rearwardly of said fifth auxiliary edge having a hexagonal cross-sectional shape defined by said pair of base surfaces and said first, second, third and fourth main surfaces.

3. A method of producing a suture needle comprising the steps of:

(a) effecting main grinding by which a distal end portion of an elongated material is ground from four directions so as to decrease the cross-sectional area of said distal end portion progressively toward a distal end of said elongated material, thereby forming on an outer periphery of said distal end portion first, second, third and fourth main surfaces arranged sequentially around the periphery of said distal end portion, said first and second main surfaces intersecting each other to form a first main edge, said second and third main surfaces intersecting each other to form a second main edge, said third and fourth main surfaces intersecting each other to form a third main edge, and at least one of said first, second and third main edges serving as a cutting edge; and (b) subsequently effecting auxiliary grinding by which that portion of said distal end portion including front ends of said first, second, third and fourth main edges is ground to form an auxiliary surface, said auxiliary surface intersecting said first, second, third and fourth main surfaces to form first, second, third and fourth auxiliary edges, respectively, said auxiliary surface intersecting said first, second and third main edges at their front ends to form first, second and third intersecting points, respectively, said second intersecting point being disposed forwardly of said first and third intersecting points, and serving as a foremost point of said suture needle, and said foremost point being connected to said first main edge via said second auxiliary edge, and also being connected to said third main edge via said third auxiliary edge.

4. A method of producing a suture needle comprising the steps of:

(a) pressing a distal end portion and a main body portion of an elongated material of a generally circular cross-section into a flattened cross-sectional shape to thereby form a pair of parallel base surfaces on opposite sides of said flattened portions;

(b) effecting main grinding by which said distal end portion of said elongated material is ground from four directions so as to decrease the cross-sectional area of said distal end portion progressively toward a distal end of said elongated material, thereby forming on an outer periphery of said distal end portion first, second, third and fourth main surfaces arranged sequentially around the periphery of said distal end portion, said second and third main surfaces intersecting one of said pair of base surfaces, said first and fourth main surfaces intersecting the other base surface, said first and second main surfaces intersecting each other at an acute angle to form a first main edge, said second and third main surfaces intersecting each other at an obtuse angle to form a second main edge, said third and fourth main surfaces intersecting each other at an acute angle to form a third main edge, said first and fourth main surfaces intersecting each other at an obtuse angle to form a fourth main edge, and said first and third main edges serving cutting edges, respectively; and (c) subsequently effecting auxiliary grinding by which that portion of said distal end portion including front ends of said first, second, third and fourth main edges is ground to form an auxiliary surface, said auxiliary surface intersecting said first, second, third and fourth main surfaces to form first, second, third and fourth auxiliary edges, respectively, said auxiliary surface intersecting said first, second and third main edges at their front ends to form first, second and third intersecting points, respectively, said second intersecting point being disposed forwardly of said first and third intersecting points, and serving as a foremost point of said suture needle, and said foremost point being connected to said first main edge via said second auxiliary edge, and also being connected to said third main edge via said third auxiliary edge.

5. A method according to claim 4, in which said auxiliary grinding is effected in such a manner that said auxiliary surface intersects said fourth main edge.

6. A method according to claim 4, in which said auxiliary grinding is effected along said fourth main edge so as to remove said fourth main edge, so that said auxiliary surface intersects said other base surface.

* * * * *